(12) United States Patent
Ben-Asouli et al.

(10) Patent No.: US 7,320,747 B2
(45) Date of Patent: Jan. 22, 2008

(54) GEL FOR ELECTROPHORESIS

(75) Inventors: Yitzhak Ben-Asouli, Kfar Hanagid (IL); Farhat Osman, Sachnin (IL)

(73) Assignee: Gene Bio-Application Ltd., Kfar Hanagid (IL)

( * ) Notice: Subject to any disclaimer, the term of this patent is extended or adjusted under 35 U.S.C. 154(b) by 0 days.

(21) Appl. No.: 11/371,313

(22) Filed: Mar. 8, 2006

(65) Prior Publication Data

US 2006/0207882 A1 Sep. 21, 2006

Related U.S. Application Data

(63) Continuation-in-part of application No. 10/422,061, filed on Apr. 23, 2003, now abandoned.

(30) Foreign Application Priority Data

Nov. 2, 2000 (IL) .................................. 139446
Nov. 2, 2000 (IL) .................................. 139447

(51) Int. Cl.
*G01N 27/447* (2006.01)
*G01N 27/453* (2006.01)
(52) U.S. Cl. ............. 204/456; 204/465; 204/469; 204/470; 204/616
(58) Field of Classification Search .......... 204/606, 204/615, 616, 620, 456, 465, 466, 469, 470
See application file for complete search history.

(56) References Cited

U.S. PATENT DOCUMENTS

| 3,803,020 A | 4/1974 | Stephan |
| 3,873,433 A | 3/1975 | Seidel et al. |
| 3,888,759 A | 6/1975 | Elson et al. |
| 3,930,983 A | 1/1976 | Sieber |
| 4,608,146 A * | 8/1986 | Penaluna ............. 204/616 |
| 4,666,581 A * | 5/1987 | Itoh et al. ............ 204/616 |
| 5,064,769 A | 11/1991 | Gambert et al. |

(Continued)

FOREIGN PATENT DOCUMENTS

DE 32 32 685 A1 3/1984

(Continued)

OTHER PUBLICATIONS

Stuart et al, Methods in Enzymology, 68, pp. 183-191, 1979.*

*Primary Examiner*—Kaj K. Olsen
(74) *Attorney, Agent, or Firm*—Martin Fleit; Paul D. Bianco; Fleit Kain Gibbons Gutman Bongini & Bianco P.L.

(57) ABSTRACT

The present invention is directed to a solidified hybrid gel for use in an electrophoresis process, having a solidified first gel portion juxtaposed with a solidified second gel portion. The first gel portion is capable of accommodating therein one or more samples for electrophoresis after said first gel portion is in solidified form, and the second gel portion is adapted for enabling an electrophoresis process to be applied to such a sample that may be accommodated in said first gel portion. Thus, the hybrid gel may be provided in a precast form to users, ready for use. The invention is also directed to methods for providing such a gel, apparatuses for accommodating such a gel, and methods for carrying out electrophoresis on a sample comprised in such a gel.

38 Claims, 10 Drawing Sheets

U.S. PATENT DOCUMENTS

| | | |
|---|---|---|
| 5,228,971 A | 7/1993 | Brumley, Jr. et al. |
| 5,443,704 A | 8/1995 | Kirkpatrick et al. |
| 5,582,702 A | 12/1996 | Cabilly et al. |
| 5,800,691 A * | 9/1998 | Kozulic .................. 204/466 |
| 5,827,418 A | 10/1998 | Haven et al. |

FOREIGN PATENT DOCUMENTS

| | | |
|---|---|---|
| EP | 0199 470 A2 | 10/1986 |
| EP | 0 471 949 A1 | 2/1992 |
| EP | 0971 229 A1 | 1/2000 |
| WO | WO/92/17259 A1 | 10/1992 |
| WO | WO 95/14921 | 6/1995 |
| WO | WO 95/20155 A1 | 7/1995 |
| WO | WO 98/10277 A1 | 3/1998 |
| WO | WO 99/30145 A1 | 6/1999 |

* cited by examiner

\* Bends that cannot be detected in 5 µl lane

10 % SDS-PAGE GeBaGel

GEL FOR ELECTROPHORESIS

CROSS-REFERENCE TO RELATED APPLICATIONS

This application is a continuation-in-part of U.S. application Ser. No. 10/422,061 filed Apr. 23, 2003 now abandoned. U.S. application Ser. No. 10/422,061 is a continuation of PCT/IL01/01001 filed Oct. 29, 2001. The contents of the related applications are herein incorporated by reference in their entirety.

TECHNICAL FIELD

The present invention relates to an apparatus for gel electrophoresis, in particular for carrying out horizontal electrophoresis with acrylamide gels. The present invention is further directed at the safe handling and disposal of such gels.

BACKGROUND

Gel electrophoresis, a commonly used method on molecular biology research, is a technique designed to separate, identify and purify DNA, RNA and protein molecules based on their weight, size and shape. This technique, which is simple and rapid to perform, is carried out by first preparing a gel. When the gel is ready it is placed in a gel box, immersed in a buffer solution, and connected to a power source. Once stimulated by the electric field that is set up in the gel, the molecules move through the gel matrix at different rates. The migration rate for each species of molecule is dependent upon the electrical charge, the size and shape of the molecules, as well as on the composition of the gel. Most commonly, the smaller molecules will move through the matrix at a quicker pace than those of a larger size. Sufficient quantity of buffer (typically TAE, TBE or protein running buffer) is generally used to ensure that the electric field is set up in the gel, and that the gel is covered with it and thus prevent the gel from drying out during electrophoresis. When loading a sample containing the molecule species of interest into the gel, a loading dye is typically used. The loading dye normally allows easy visualization of the solution during the loading process, as well as enabling the density of the sample to be increased to ensure that the sample is fully and evenly accommodated in a corresponding well in the gel, and further allows visualisation of the migration during electrophoresis.

The most commonly used gels are prepared with either agarose or acrylamide, either one of which can be provided in varying shapes, sizes and thicknesses. The deciding factor as to which particular gel and its physical attributes is generally related to the size of molecule being separated.

Acrylamide is usually chosen for relatively small molecules such as proteins, while agarose is used for larger molecules such as DNA or RNA. In any case, while agarose is the preferred choice for horizontal gel electrophoresis, being cast in typically open trays, acrylamide is used typically used only for vertical gel electrophoresis, being cast between two glass plates, and is not used for horizontal electrophoresis in the art. The reason for this is that acrylamide does not tend to provide a mechanically stable well structure because the acrylamide gel is very elastic and its thickness is very thin (up to 1.5 mm), and if used for horizontal gel electrophoresis adjacent wells tend to cave in negating any possibility to load samples therein. When acrylamide gels are used in vertical electrophoresis, the depth dimension of the wells is aligned with the electric field, and relatively deep and narrow wells may be provided which are substantially well-spaced with respect to neighbouring wells. Furthermore, in vertical electrophoresis the wells are created between two parallel spaced vertical glass plates, which by providing two opposed walls for each well enable the wells to remain stable. However, vertical gel electrophoresis is not without problems. For example, it is easier to load samples into horizontal gel wells than in vertical gel wells. It is also difficult to cast vertical acrylamide gels, particularly gradient gels, and special loading tips for the samples are required. In vertical gel electrophoresis, one buffer tank is vertically spaced from the other buffer tank, and it often occurs that running buffer will leak from the upper tank to the lower tank; eventually, the upper tank gets drained of buffer severing electrical connection between the upper electrodes and the gel.

Unpolymerised acrylamide is a potent neurotoxin and is absorbed through the skin. The effects of acrylamide are cumulative. Although polymerised acrylamide is considered to be non-toxic, it should nevertheless be handled with care because of the possibility that it may contain small quantities of unpolymerised acrylamide. Thus, contact with users must be strictly avoided, particularly when the acrylamide is unpolymerised and/or is in powder form, during handling and when disposing of the gels after use.

It is therefore an aim of the present invention to provide a device and method which overcomes the limitations of prior art electrophoresis devices and methods.

It is another aim of the present invention to provide an acrylamide-based gel that may be used for horizontal electrophoresis.

It is another aim of the present invention to provide a device for enabling safe handling and disposal of such gels which may contain harmful substances.

It is another aim of the present invention to provide such a device that is simple to use.

It is another aim of the present invention to provide such a device that is relatively simple mechanically and thus economic to produce.

These and other aims are accomplished in the present invention by providing a precast-gel cassette for horizontal electrophoresis, in particular a disposable and closed cassette for horizontal electrophoresis. In particular, the cassette enables the use of acrylamide gels in horizontal electrophoresis. This is accomplished by precasting a transverse strip of agarose in ionic communication with the main body of acrylamide gel within the cassette. The agarose strip enables stable wells to be formed therein (by means of a comb, for example) for insertion of samples therein. Such a agarose/acrylamide hybrid gel combination is often difficult to cast in situ by users, and the acrylamide portion thereof poses safety issues during handling and disposal of the gel. Accordingly, the present invention further provides significant advantages to users wishing to use acrylamide gels for horizontal electrophoresis, since the cassette comes prepared with precast acrylamide gel and agarose gel included therein.

In another aspect of the invention, the cassette comprises at least one and preferably a pair of agarose plugs one at each longitudinal open end of the cassette. The plugs essentially isolate the acrylamide gels from the outside of the cassette, thereby minimising any possibility of human contact with the acrylamide gel in the cassette. This is an important safety feature, particularly in view of the disposability of the cassette, which thus minimises any handling of toxic substances.

In the preferred embodiment, the cassette comprises a box-like construction, having a bottom flat base and four vertical walls joined thereto about its periphery, and an upper cover mountable onto the vertical walls to define a gel chamber into which gel may be precast. The cassette also comprises openings at two opposite ends of the bottom base to enable ionic communication between the gel and an electrolytic solution in which the cassette may be partially immerged. The openings are preferably comprised in hollow legs running the transverse length of the cassette at two longitudinal ends thereof, the legs comprising gel in ionic communication with the main body of gel within the cassette. This design is particularly adapted for using the cassette with standard ion exchange chambers. An agarose/acrylamide hybrid gel is provided within the chamber for performing horizontal electrophoresis, and agarose gel is provided in the legs to provide ionic communication between the hybrid gel and the external buffer solutions, while at the same time providing a safety barrier between the acrylamide gel within the cassette and the outside thereof.

U.S. Pat. No. 3,888,759 discloses a gel cassette having a substantially box-like construction, having a downwardly depending transversely extending hollow leg at each longitudinal end of the cassette. The device appears to be reusable, providing the user with different options, and it appears intended for the user to cast the gel each time, rather than providing a precast package. There is, however, no disclosure or any indication of providing a hybrid gel for enabling horizontal electrophoresis with an acrylamide gel.

U.S. Pat. No. 5,443,704 discloses a substantially box-like container assembly for an electrophoresis gel, containing more than one precast gel deposited therein. However, the different gels are provided in a stacked arrangement, which does not provide the advantages of the present invention at least in terms of enabling an acrylamide gel to be used for horizontal electrophoresis in combination with a juxtaposed agarose strip comprising then wells.

U.S. Pat. No. 5,064,769 discloses a gel for immunoassay of a single protein species in which the horizontal gel comprises a first part made from acrylamide gel having a proportion of agarose (0.7%) sufficient to enable stable wells to be formed therein. The first part of the gel is juxtaposed with a second part made from agarose gel. Acrylamide gel is used in this reference only to eliminate diffusion effects in the wells, and is not used, nor can it be used successfully, to form the wells—this is accomplished by the 0.7% agarose. Use of the agarose gel in the second part of the gel combination is well known for horizontal electrophoresis. The gel arrangement provided by this reference is in fact the opposite way round to the present invention, and thus teaches away from the present invention. There is no disclosure or suggestion regarding using acrylamide for horizontal gel electrophoresis, or of using agarose therewith for providing the wells.

In U.S. Pat. No. 3,930,983 an arrangement and process are disclosed for determining antigens, in which a support plate is coated with an agar or agarose as a matrix in successive gel strips. However, there is no disclosure or suggestion that other than the first strip containing the wells the other strips should be made from acrylamide gel rather than agarose. In fact, it appears that the gel should be the same for all the strips, the only variable being the monospecific antiserum contained in each of the strips.

U.S. Pat. No. 5,582,702 is directed to a self-contained electrophoresis apparatus comprising a housing having a gel body accommodated therein together with ion exchange matrices and electrodes, which are electrically connectable to an external power source. The apparatus is thus not generally compatible with existing ion exchange chambers currently used for horizontal electrophoresis. While it is stated therein that the gel may be from agarose or acrylamide, there is no disclosure or suggestion of how to overcome the well integrity problem encountered with acrylamide gels when it is attempted to use the same for horizontal electrophoresis. In particular, this problem is not addressed by the reference, and there is no disclosure or suggestion of how to overcome the same, less so in the manner of the present invention.

WO 95/20155 relates to a sample holder in the form of a well, into which a sample and a first molten gel is introduced. When the first gel/sample mixture has solidified, the sample holder is applied against one end of a second gel slab, such as to bring the first gel/sample solidified mixture in ionic contact with the second gel. At no time is the first gel in solidified form brought into contact with the second gel prior to introducing the sample. Thus, the first gel is in no way adapted for accommodating the sample therein when in the solidified state, and thus neither discloses nor anticipates the present invention. The method and apparatus disclosed by the patent still requires the first gel to be cast (mixed with sample), and further manipulation thereof, in contrast to the present invention in which the first gel and the second gel may be precast, and are ready (when solidified) to accommodate therein samples, typically via wells in the first gel.

WO 99/30145 relates to a slotted electrophoresis gel composition and methods for use, for providing a multilayered gel for vertical gel electrophoresis. It does not address, nor provide a solution for, the problem of forming stable sample wells for horizontal electrophoresis in an acrylamide gel. Specifically, it does not disclose nor suggest a hybrid gel as in the present invention, but merely a slotted gel structure having at least three layers:—two primary gel layers on either side of a slotted second gel layer.

EP 471949 discloses a capillary tube for performing capillary zone electrophoresis. The tube is modified by including a polystyrene frit that divides the tube into a downstream free zone, and an upstream zone which can comprise a polyacrylamide stacking gel. The gel plug functions as a filter to pre-treat the samples that are to be analysed in the free zone of the tube.

WO92/17259 describes a method for identifying a solute of interest in an effluent stream. A sample containing the mixture to be separated is passed through a first system capable of partitioning the components of the mixture, and a detector provides a first output that describes the temporal and/or spatial sequence of components exiting the first system. The effluent stream is then passed through a second system capable of extracting a solute of interest from the effluent, and a detector provides a second output that describes the temporal and/or spatial sequence of components exiting the second system, which no longer includes the solute of interest. The solute of interest can then be identified in the first output by comparing this to the second output. This method is thus directed at identifying a substance in a first separating system by employing a parallel second separating system.

Other publications of background interest include EP 971229, U.S. Pat. No. 5,228,971, WO 95/14921, DE 3232685, EP 199470, U.S. Pat. Nos. 5,827,418, 3,803,020, WO 98/10277 and U.S. Pat. No. 3,873,433.

SUMMARY OF THE INVENTION

The present invention relates to a solidified hybrid gel for use in an electrophoresis process characterised in comprising at least a first solidified gel portion juxtaposed with at least a solidified second gel portion, wherein said solidified first gel portion is capable of accommodating therein at least one sample for electrophoresis after said first gel portion is in solidified form, and the second gel portion is adapted for enabling an electrophoresis process to be applied to such a sample that may be accommodated in said first gel portion. Typically, the first gel portion is particularly adapted to enable a sample accommodated therein to migrate freely to said second gel portion. In particular, the first gel portion comprises at least a proportion of agarose for enabling accommodating therein at least one sample for electrophoresis, and the second gel portion comprises acrylamide. Preferably, the hybrid gel is for use with a horizontal electrophoresis process, and the first gel portion is adapted for accommodating therein at least one sample for electrophoresis by means of at least one corresponding well formed in said first gel portion.

The hybrid gel is preferably accommodated in a suitable chamber provided by a casting tray, and a top cover adapted to engage with the said tray may be optionally provided. The tray typically comprises a base having a pair of longitudinally spaced openings, a first opening providing communication between the first gel portion and an outside of the tray, and the second opening providing communication between the second gel portion and an outside of the tray.

The present invention also relates to an apparatus for performing electrophoresis therein, comprising:

a housing comprising at least a base and peripherally joined walls defining a first chamber having a first longitudinal end and a second longitudinal end;

a hybrid gel according to the present invention accommodated in said first chamber arranged such that migration occurs in a direction from said second end to said first end when said device is used in an electrophoretic process;

wherein said base comprises at least one first opening and at least one said second opening respectively at said first and second longitudinal ends thereof, each said opening adapted to permit ionic communication between said gel and an external ionic buffer solution.

Preferably, the apparatus further comprises substantially hollow first and second transverse legs downwardly depending therefrom at said first and second longitudinal ends thereof, respectively, said first and second legs comprising a suitable third gel portion and a suitable fourth gel portion, respectively, in communication with said first chamber via said corresponding openings, said first and second legs having open bottom ends.

The apparatus may further comprise a first acrylamide barrier in communication with said first opening for substantially preventing contact between at least said second portion of said hybrid gel and an outside of the apparatus via said first opening. This first acrylamide barrier may be comprised by said first gel portion of said hybrid gel, said first portion being comprised substantially of agarose. Additionally or alternatively, the first acrylamide barrier is provided by said third gel portion comprised in said first leg, and the third gel portion may comprise agarose.

The base may further comprise a lower part and an upper part, thereby defining a stepped bottom base. The lower part is joined longitudinally to the upper part by an intermediate wall. Optionally, the intermediate wall is perpendicular to the lower part of the base. Alternatively, the intermediate wall is positioned at an incline from the lower part of the base to the upper part of the base. Alternatively, the intermediate wall ascends arcuately from the lower part of the base to the upper part of the base. Preferably, the intermediate wall meets the upper part of the base at a point on said base that is located below the second gel matrix.

Preferably, the apparatus further comprises a second chamber juxtaposed and in communication with said first chamber, said second chamber adapted for providing at least part of said first acrylamide barrier. The second chamber may comprise a fifth gel portion, typically agarose.

The apparatus may optionally further comprise a second acrylamide barrier in communication with said second opening for substantially preventing contact between at least said second portion of said hybrid gel and an outside of the apparatus via said second opening. Typically, the second acrylamide barrier is comprised by a sixth gel portion interposed between said second gel portion of said hybrid gel and said second opening, said sixth gel portion being comprised substantially of agarose. Alternatively or additionally, the second acrylamide barrier may be provided at least in part by said fourth gel portion comprised in said second leg, said fourth gel portion typically comprising agarose.

Preferably, the apparatus further comprises a cover for releasably closing at least said first chamber, and typically further comprises a suitable comb for forming said wells, said cover comprising at least one suitable aperture for enabling said comb to penetrate into said first gel portion. The cover may further comprise a tab in registry with and spaced from a platform comprised at said first longitudinal end of said apparatus.

Preferably, suitable adhesive strips are provided for reversibly sealing said bottom ends of said first and second legs, respectively.

Advantageously, the base and said first and second legs are adapted to enable said apparatus to be used with standard electrophoresis devices having a pair of parallel juxtaposed buffer-containing toughs separated by an elevated platform for supporting the said base, said first and second legs extending sufficiently into corresponding said troughs to provide ionic communication at least between said third gel portion and buffer contained in one trough, and between said fourth gel portion and buffer contained in the other trough.

The present invention also relates to a method for providing a hybrid gel comprising a first gel portion in communication with a second gel portion according to the present invention. The method may comprise the following steps:

(a) providing a closed tray having a pouring aperture, and turning the tray vertically such that the aperture is uppermost;

(b) pouring said first gel portion via said aperture up to a required height therein and allowing said first portion to set;

(c) pouring said second gel portion therein up to the top of the tray, and allowing said second portion to set;

(d) returning said tray to a horizontal orientation.

Alternatively, the method may comprise the following steps:

(a) providing an open tray;

(b) providing a temporary transverse retaining wall within the tray, displaced longitudinally with respect to one longitudinal end thereof, to define a subchamber therebetween;

(c) pouring said first gel, portion into said subchamber and allowing the first gel portion to set;

(d) removing the temporary retaining wall;
(e) closing the tray by means of a suitable cover having a suitable aperture;
(f) pouring the second gel portion into the remainder of the tray via said aperture and allowing the second gel portion to set.

The method preferably comprises the step of forming at least one well in said first gel portion. The wells may be formed by means of a comb, via suitable apertures in the tray, or alternatively by means of a comb by first removing an upper cover of the tray.

The present invention also relates to a method for carrying out a horizontal electrophoresis process on at least one sample comprising the steps of:
(a) providing a hybrid gel matrix comprising at least a first gel portion juxtaposed with at least a second gel portion, according to the present invention, said first gel portion comprising at least one well formed therein, each said well adapted to receive a corresponding sample;
(b) accommodating said gel matrix in a suitable horizontal electrophoresis chamber;
(c) accommodating said at least one sample within a corresponding at least one well in said first gel portion;
(d) providing suitable buffer solution to said chamber;
(e) providing a suitable electric potential to said chamber such as to activate the electrophoresis process.

Typically, the sample may comprise small fragments of nucleic acids including at least one of DNA and RNA, or at least one suitable protein.

Lanes: (1) Molecular weight marker (11-170 kDa), (2) 0.1 µg BSA and 0.1 µg lysozyme, (3) 0.2 µg BSA and 0.2 µg lysozyme, (4) 0.3 µg BSA and 0.3 µg lysozyme, (5) 0.4 µg BSA and 0.4 µg lysozyme, (6) 0.8 µg BSA and 0.8 µg lysozyme and (7) 1.6 µg BSA and 1.6 µg lysozyme.

Abbreviations: MW: molecular weight; kDa: kilodaltons.

Figure 12:
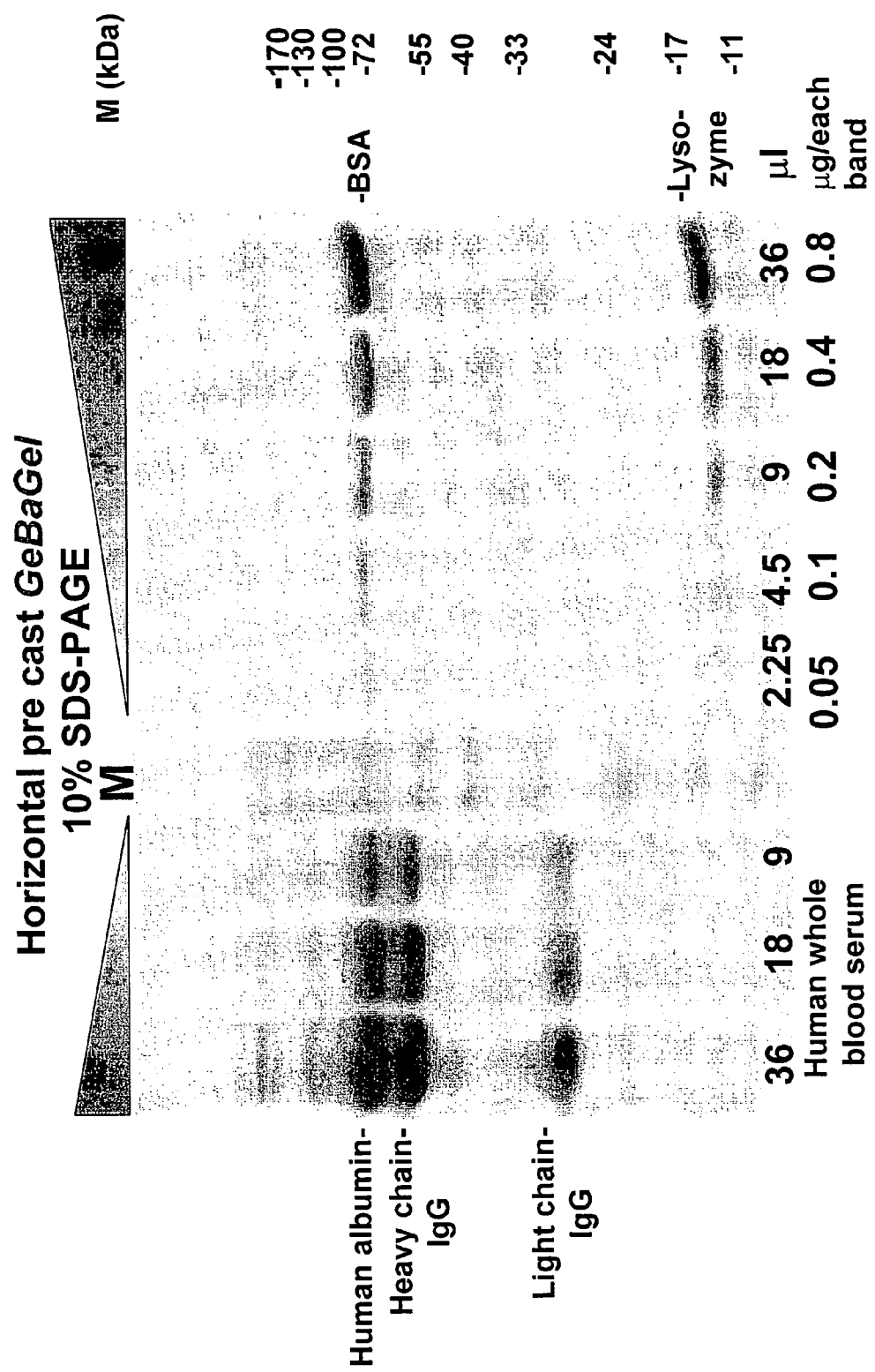

FIG. 12 shows the quantitative and qualitative advantages of horizontal PAGE gels and the effect of sample volume on the experiment results. Human serum, bovine serum albumin (BSA) and lysozyme were separated on a horizontal pre cast 10% SDS PAGE GeBaGel of the invention.

Lanes: (1) human serum, (2) human serum 1:2 dilution (3) human serum 1:4 dilution, (4) Molecular weight marker (11-170 kDa), (5) 0.05 µg BSA and 0.05 µg lysozyme, (6) 0.1 µg BSA and 0.1 µg lysozyme, (7) 0.2 µg BSA and 0.2 µg lysozyme, (8) 0.4 µg BSA and 0.4 µg lysozyme and (9) 0.8 µg BSA and 0.8 µg lysozyme.

Abbreviations: MW: molecular weight; kDa: kilodaltons, HA: human albumin; H-IgG: immunoglobulin G heavy chain; L-IgG: immunoglobulin G light chain.

Figure 13:
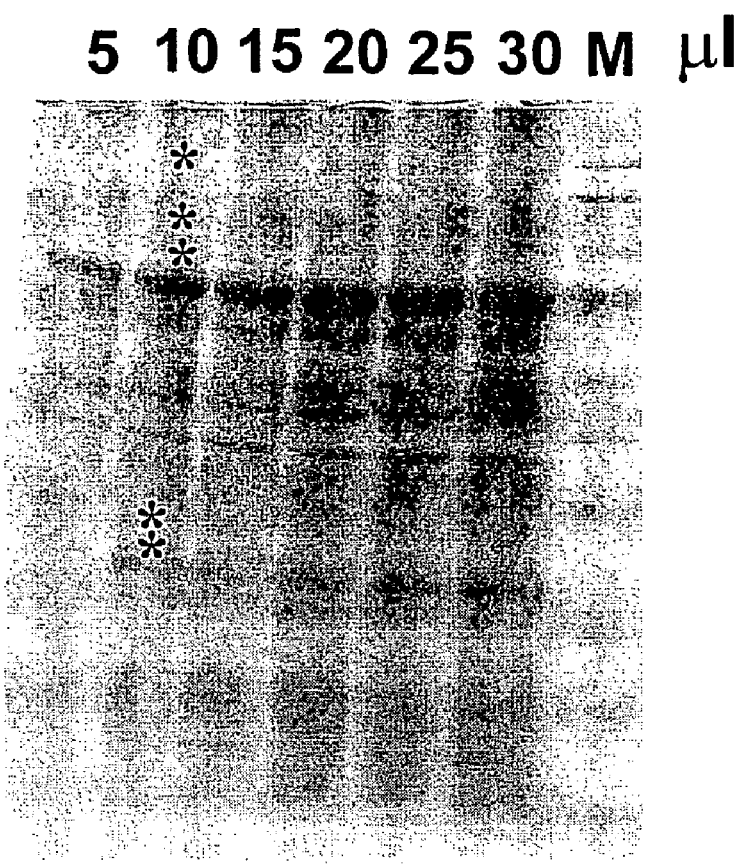

FIG. 13 shows the quantitative and qualitative advantages of horizontal PAGE gels and the effect of sample volume on the ability of visualizing different bands. Incremental volumes (5-30 µl) of E. coli JM109 extract samples were loaded on a horizontal pre cast 10% SDS PAGE GeBaGel of the invention. Gel was subjected to coomassie blue staining for bands visualization.

DISCLOSURE OF THE INVENTION

The present invention is defined by the claims, the contents of which are to be read as included within the disclosure of the specification, and will now be described by way of example with reference to the accompanying Figures.

In the present application the word acrylamide is to be understood as relating also to polyacrylamide, bispolyacrylamide acrylamide based gels and the like, in addition to its normal meaning or in lieu thereof.

The present invention relates to a solidified hybrid gel matrix for use in an electrophoresis process, in particular a horizontal electrophoresis process, and to methods for preparing such gels.

By solidified is meant herein that the gel matrix is no longer in a molten state, and has "set", "hardened" or "gelled" in a manner known in the art.

Figure 1:
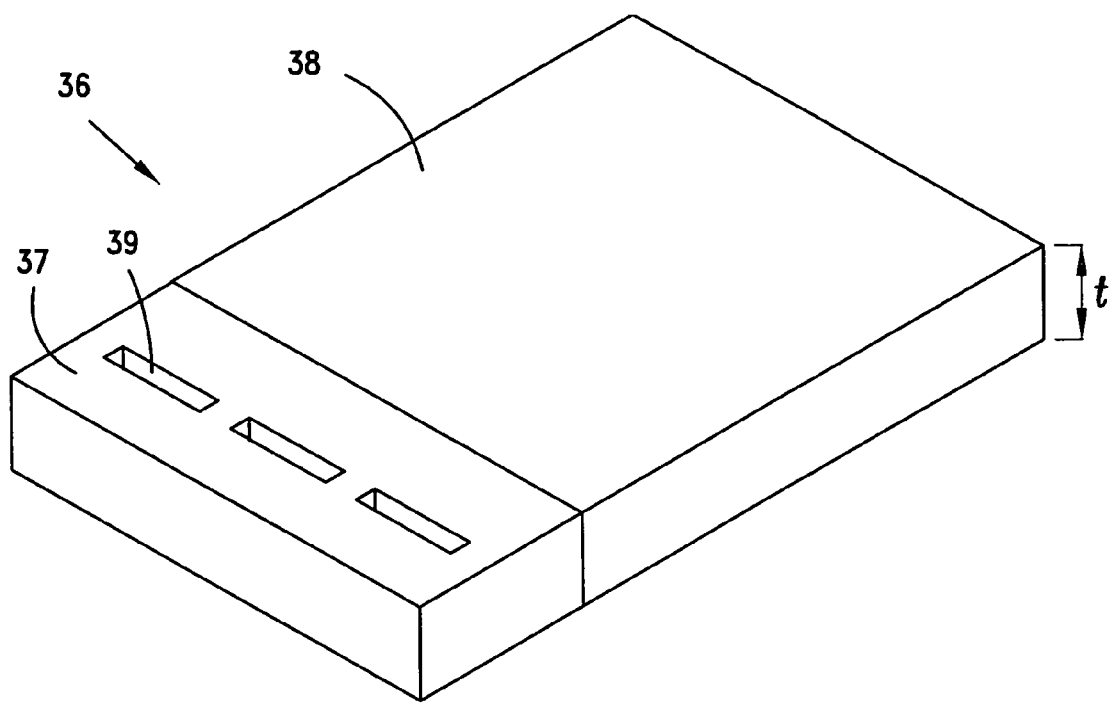
FIG. 1 shows in perspective view the main elements of the hybrid gel according to a preferred embodiment of the present invention.

Referring to FIG. 1, the hybrid gel according to a preferred embodiment thereof, generally designated by the numeral (36), is typically in the form of a solidified slab, having a thickness (t), and is characterised in being comprised of a first portion and a second portion juxtaposed one to the other and at least in mutual ionic contact when undergoing an electrophoresis process. The first portion (37) is adapted, when in the solidified state, for subsequently accommodating therein at least one sample to be electrophoresed, and thus comprises at least one and preferably a plurality of wells (39). As such, the first portion (37) is made preferably from agarose, though it need only comprise sufficient agarose to provide a stable well structure when solidified, and subsequently when loaded with a sample and during horizontal electrophoresis. In the latter case in particular, i.e., when the first portion only comprises small amounts of agarose, the first portion may also comprise other materials including other types of gels, so long as this portion still provided a stable well structure and does not block the migration of molecules form the wells. There are also other less suitable substances derived from agar which, while providing stable wells do not enable the efficient migration of molecules. The second portion (38) is made from acrylamide, or substantially therefrom, and is juxtaposed with the first portion such as to enable ionic communication between the two portions, as well as to enable molecules migrating from the wells (39) in the first portion (37) to continue migrating through the second portion (38). Thus, the hybrid gel (36) according to the present invention enables horizontal electrophoresis of samples in which the preferred gel is acrylamide or acrylamide-based gels, in applications, for example, such as the separation of small nucleic acids (DNA and RNA), or proteins (using SDS-acrylamide gel in the second portion (38).

Typically, the first portion (37) and the second portion (38) are arranged in series, and may be provided in solidified form pre-cast in suitable trays, or may be cast in-situ as required. In most cases, the first portion (37) is cast first, and this may be done by providing a closed tray having a pouring aperture, and turning the tray vertically such that the aperture is uppermost. The first gel portion, typically agarose, is then poured in the molten or fluid state into the tray via the aperture up to the required height, and when set the second gel portion, typically acrylamide gel is then poured to the top of the tray. When both gels are set, i.e. solidified, the tray may be turned back to its normal horizontal orientation, and suitable wells (39) formed therein, typically by means of a comb, via suitable apertures in the tray, or by first opening the top of the tray. Alternatively, the second portion (38) may be cast first while the closed tray is vertical, by pouring the acrylamide to the required height through the aperture. The tray is then turned back to the horizontal orientation, and the agarose is pored in the remainder of the tray, and suitable wells (39) are formed therein as before.

Alternatively, the hybrid gel (36) may be cast in an open tray by first providing a temporary transverse retaining wall within the tray, displaced longitudinally with respect to one longitudinal end thereof, to define a subchamber therebetween into which agarose gel is poured and set. Next, the temporary retaining wall is removed, and the tray is closed via a suitable lid, and acrylamide gel is poured into the remainder of the tray, typically to the same level as the agarose in the first gel portion (37) to form the second gel portion (38). The second gel portion (38) is thus in contact with the first gel portion (37). Wells (39) may be provided in the normal manner, for example as described above.

Figure 2:
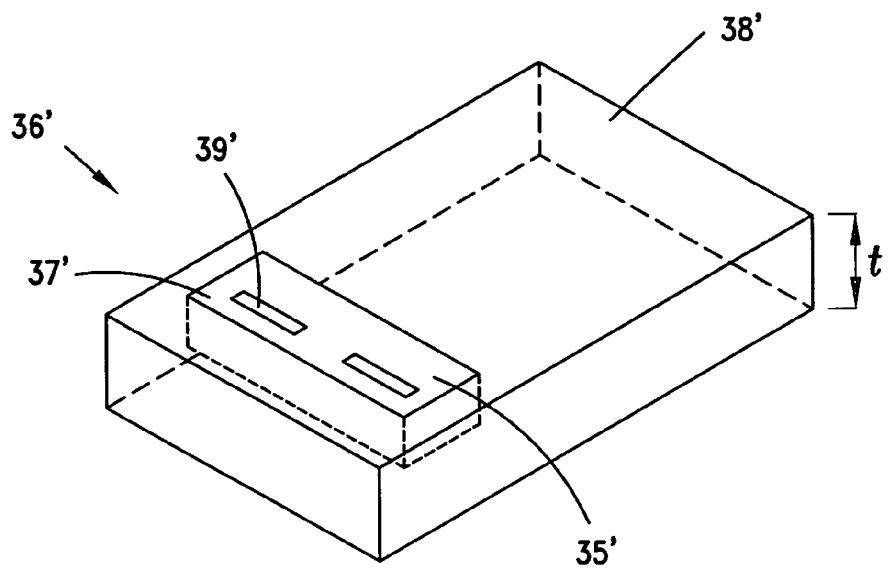
FIG. 2 shows in perspective view the main elements of the hybrid gel according to a second embodiment of the present invention.

Typically, the first portion (37) and the second portion (38) are provided in two serially juxtaposed portions, as described above with reference to FIG. 1. Nonetheless, other configurations are also possible. For example, and referring to FIG. 2, in a second embodiment of the hybrid gel (36'), the first portion (37') could be provided as a "plug" (35') of agarose (or similar) gel having suitable wells (39'), the plug (35') being surrounded by a second portion (38') of acrylamide (or similar) gel.

For electrophoresis of small fragments of nucleic acids (DNA and RNA), the gel thickness (t) of at least the second portion (38) is typically from about 0.3 mm to about 4 mm, while for the electrophoresis of proteins the corresponding gel thickness (t) is typically from about 1 mm to about 2 mm.

While typically the first gel portion (37) has substantially the same thickness as the second gel portion (38) this need not necessarily be so for all embodiments of the hybrid gel (36).

The present invention also relates to a device, or apparatus, and method for horizontal electrophoresis based on such a hybrid gel (37), comprising a first portion comprising an agarose gel in juxtaposition with a second gel portion comprising an acrylamide gel, in which the first portion is adapted for receiving samples that are to undergo horizontal electrophoresis. In particular, the present invention also relates to a cassette-type device containing such a hybrid gel, the gel being preferably pre-cast therein. Preferably, such a cassette is also provided with suitable traps for minimising contact of the acrylamide gel with the external environment including users. Such traps typically comprise a barrier gel substance like agarose which isolates the acrylamide gel from the outside of the cassette thereby minimising any possibility of human contact with the acrylamide gel in the cassette. This gel substance contains an electrolytic solution to enable ionic communication between the gel and the external electrolytic solution.

Such an apparatus is preferably disposable, but may also be re-usable for a host of applications. The term "disposable" in the present application means that the devices are designed (in corresponding embodiments) to be thrown away or otherwise disposed off after one use with only negligible economic loss. Such negligible economic loss may be comparable, for example, to the economic loss incurred, in disposing of plastic pipettes for handling liquids or eppendorf tubes. While these items may be used more than once, they are nonetheless typically thrown away after a single use, this being more cost effective than cleaning and/or sterilising the same for subsequent use.

Referring to the Figures, FIGS. 2 to 6 illustrate a preferred embodiment of the present invention. The apparatus or cassette, designated by the numeral (1), comprises a housing (100) of a box-like construction, comprising a first chamber (30) adapted for accommodating a hybrid gel (36) for electrophoresis. Optionally, a barrier substance is accommodated in a second chamber (40). Such a barrier substance may comprise a substance adapted for providing an acrylamide barrier, i.e., a barrier for separating acrylamide in the hybrid gel (36) from the outside of the cassette (1). Alternatively, the barrier substance may comprise an absorbtion material capable of retaining therein at least one target substance migrating thereto from the hybrid gel (36), and preventing such a target substance from exiting the cassette (1), and described more fully in co-pending Israel Patent Application No. 139447, the contents of which are herein incorporated by reference in their entirety.

Figure 3:
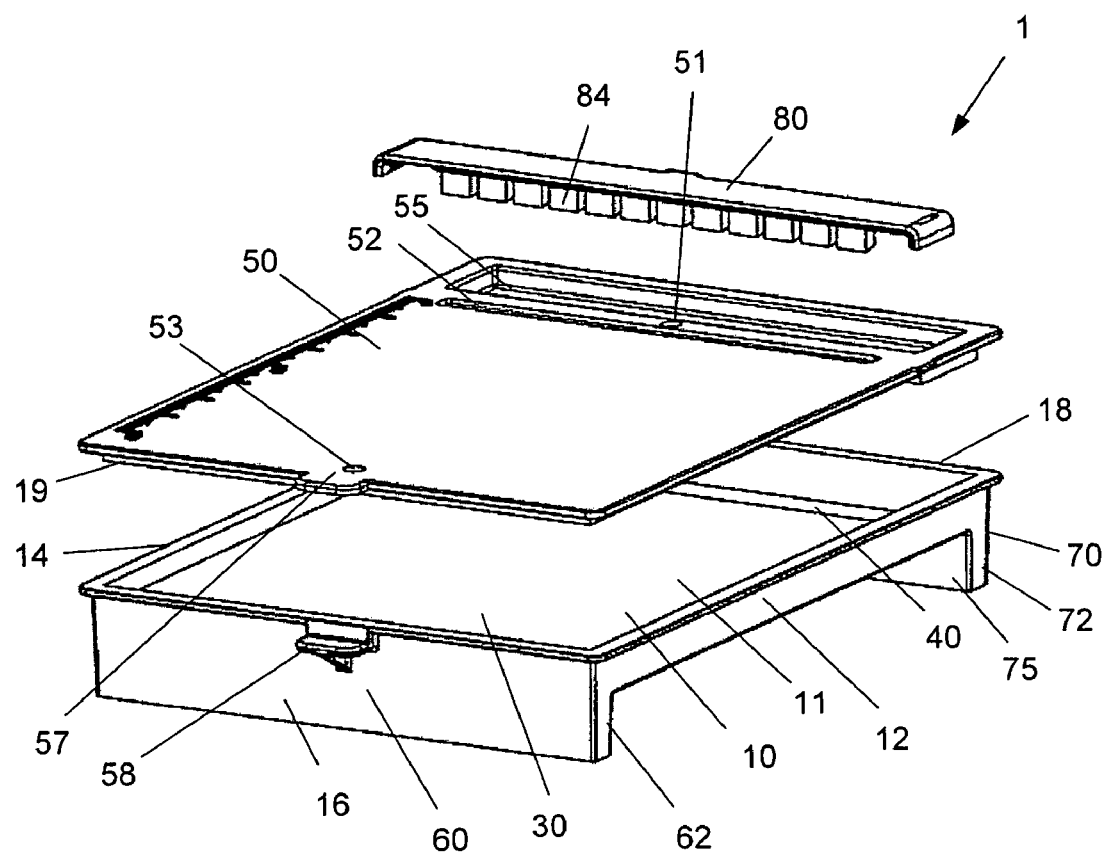
FIG. 3 shows in exploded perspective view the main elements of a preferred embodiment of the apparatus of the present invention.
Figure 4:
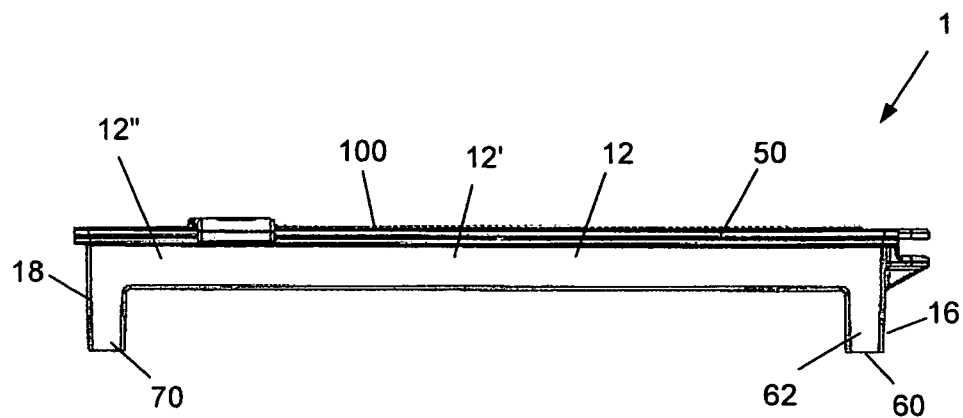
FIG. 4 shows in side view the embodiment of FIG. 3 assembled.
Figure 5:
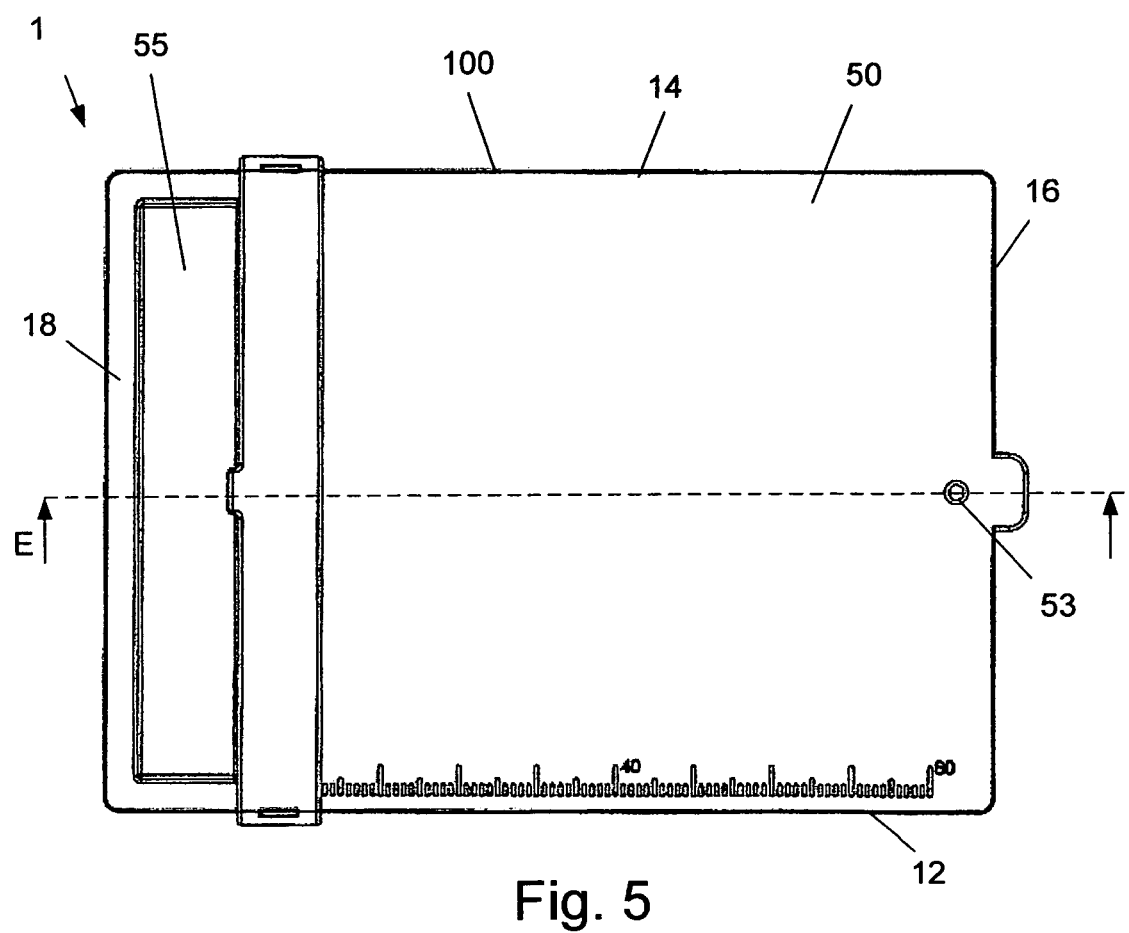
FIG. 5 shows in top view the embodiment of FIG. 4.
Figure 6:
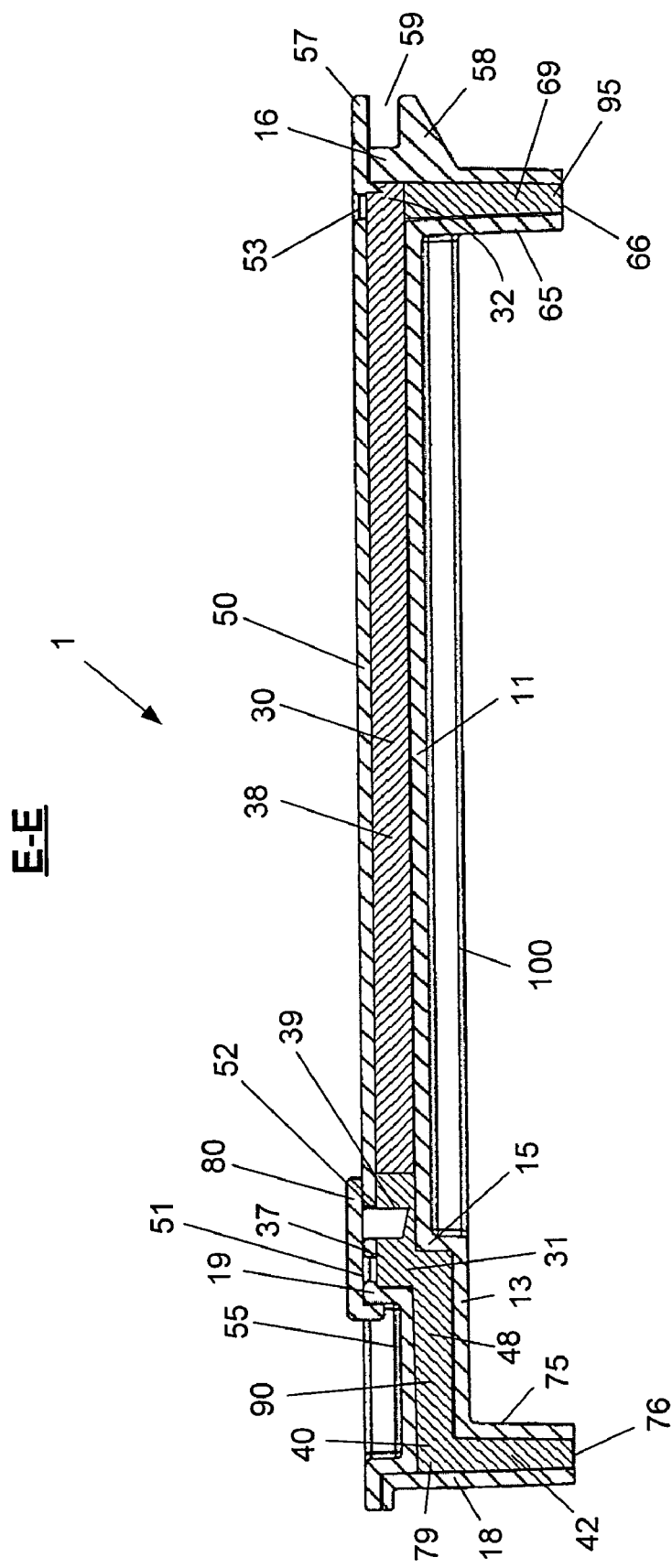
FIG. 6 shows in side elevational cross-sectional view, the embodiment of FIG. 5 taken along E-E, comprising a hybrid gel according to the embodiment of FIG. 1.

The cassette (1) comprises a stepped bottom base (10) having a flat upper part (11) and a flat but shorter lower part (13) joined longitudinally one to the other by a first intermediate vertical wall (15). Two side walls (12), (14) run the longitudinal length of the cassette and are preferably integrally joined to the base (10) and to end walls (16) and (18) at opposite longitudinal ends of the cassette (1). A second intermediate wall (19) is joined to side walls (12) and (14) at a longitudinal location between first intermediate wall (15) at the end wall (18) closest thereto. The second intermediate wall (19) substantially divides each side wall (12) and (14) longitudinally into longer portions (12') and (14'), respectively, extending between the end wall (16) and intermediate wall (19), and shorter portions (12") and (14"), respectively, extending between the intermediate wall (19) and the other end wall (18). The upper edge of the second intermediate wall (19) is substantially coplanar with the upper edge of end wall (16) and with the upper edges of at least the longer side wall portions (12') and (14'), and thus enable an upper cover (50) to be releasably and sealingly mounted thereonto. Upper cover (50) may comprise optionally closable apertures (51) and (53) longitudinally spaced one from the other along the mid-line of the cover (50). These apertures (51), (53) facilitate pouring of gel into the cassette (1) when the cover (50) is in place, described in greater detail hereinbelow. Thus, the second intermediate wall (19), end wall (16) and the longer side wall portions (12') and (14'), together with upper cover (50) and the upper part (11) of the base (10) define the first chamber (30) of the cassette (1). The second chamber (40) of the cassette is correspondingly defined by the second intermediate wall (19), end wall (18) and the shorter side wall portions (12") and (14"), together with upper wall (55) and the lower part (13) of the base (10). Upper wall (55) may optionally be joined typically integrally with the first intermediate wall (15), end wall (18) and the shorter side wall portions (12") and (14"). Preferably, though, and as illustrated in FIGS. 3 and 6, upper wall (55) is integrally joined to the upper cover (50) and is releasably and sealingly mountable onto the upper edges of the second intermediate wall (19), end wall (18) and the shorter side wall portions (12") and (14"). The lower edge of the second intermediate wall (19), however, does not extend as far as the lower part (13) of the base (10), and thus communication between the first chamber (30) and second chamber (40) is provided by virtue of the longitudinal gap between the first and second intermediate walls, (15) and (19), respectively.

Thus, in the preferred embodiment of the apparatus, the first chamber (30) is partially superposed over the second chamber (40), defining an area (31) where the two chambers overlap horizontally. At least a portion of this area (31) has an opening, or preferably is open, providing communication between the first chamber (30) and the second chamber (40).

FIG. 6 shows first intermediate wall (15) as being located below the well (39), on the side closer to second intermediate wall (19). However, first intermediate wall (15) can optionally be located longitudinally farther away from second intermediate wall (19). Nevertheless, first intermediate wall (15) must meet the upper part (11) at a point that is located longitudinally below the second gel matrix.

Preferably, the cassette (1) or other embodiments thereof is provided with a suitable hybrid gel matrix (36) accommodated in the first chamber (30) according to the present invention. A suitable barrier substance, typically in the form of a second gel matrix (48), is accommodated in the second chamber (40) and may also be provided pre-cast within the cassette (1). Alternatively, the cassette (1) or other embodiments thereof may be provided without one or both these gels, which can be cast as and when needed. In any case, the hybrid gel matrix (36) is adapted for performing horizontal electrophoresis therein. The second gel matrix (48) is typically adapted for providing a barrier between the acrylamide comprised in the hybrid gel (typically in the second portion (38), but sometimes also comprised in the first portion (37)), preventing contact therewith via the opening (42), while at the same time allowing ionic communication between the outside of the cassette and the hybrid gel (36) via the second gel matrix (48) and the opening (42).

Top cover (50), and preferably the rest of housing (100) is made from any suitable ultraviolet-transparent material. Preferably, the whole of the cassette (1), in particular the housing (100), is made from an economically disposable material.

Optionally, a tab (57) is provided at one end of the cover (50), and a corresponding platform (58) is provided at end (16), preferably integrally joined thereto, such that the tab (57) is in registry with platform (58) and mutually spaced by space (59) when the cover (50) is in place over chamber (30). By placing a suitable flattened tool such as a screwdriver or key (not shown), for example, within space (59) and rotating it by 90°, say, the cover (50) may be snapped open and thus removed from the chamber (30).

Having an openable cover (50) is important in applications, for example, where it is required to remove some of the second gel portion (38) for further processing such as electroelution or transfer of molecules from the second gel portion (38) to a membrane (western blot or northern blot).

The cassette (1) also comprises openings at two opposite ends of the bottom base (10) to enable direct or indirect ionic communication between the hybrid gel (38) that is accommodated in the cassette (1) and an electrolytic solution in which the cassette (1) may be partially immersed. Thus, transverse opening (32) at longitudinal end of the upper part (11) of the base (10) near end wall (16) provides communication between the first chamber (30) and the outside of the cassette (1). Similarly, transverse opening (42) at longitudinal end of the lower part (11) of the base (10) near end wall (18) provides communication between the second chamber (40) and the outside of the cassette (1).

Openings (32) and (42) serve to provide ionic communication between the gels accommodated within the cassette (1) and external ionic solutions, and thus enable electrophoresis to be conducted within the cassette (1) with the provision of a suitable electric field. Preferably, though, the openings at the bottom base (10) are in the form of substantially hollow leg members running the transverse length of the cassette (1) at two longitudinal ends thereof, the leg members also being capable of accommodating gel in ionic communication with the main body of gel accommodated within the cassette (1). This inverted-U design is particularly adapted for using the cassette (1) with standard ion exchange chambers, which are generally in the form of two juxtaposed buffer-containing troughs separated by an elevated platform which is ideal for supporting the base (10) of cassette (1). One leg member extends downwardly into one trough, and the other leg member into the second trough to provide ionic communication at least between the gel contained in the legs and the corresponding buffer solutions in the troughs, and between the gels in the leg members via the hybrid gel (36) and the second gel matrix (48). One trough has a cathode and the other trough has an anode.

Thus, the cassette (1) optionally, and preferably, comprises hollow legs (60) and (70) provided at opposite longitudinal ends thereof. At one end of the cassette (1), leg (60) is defined by a downwards extension of end wall (16), together with downwardly extending tab-like projections (62), (64) at the end of longer side wall portions (12") and (14"), respectively, and a fourth wall (65) projecting downwards from the upper part (11) of base (10). Similarly, leg (70) at the other longitudinal end of the cassette (1) is defined by a downwards extension of end wall (18), together with downwardly extending tab-like projections (72), (74) at the end of shorter side wall portions (12') and (14'), respectively, and a corresponding fourth wall (75) projecting downwards from the lower part (13) of base (10). Each leg (60), (70) is open at the corresponding bottom end, (66) and (76) respectively, thereof, which may be temporarily closed (at least prior to use of the cassette (1)) by means of suitable removable adhesive strips (not shown) adhered thereto. The bottom ends (66), (76) are in communication with the first chamber (30) and second chamber (40), respectively, via the transverse openings (32) and (42), respectively.

As mentioned hereinbefore, the first chamber (30) is adapted to accommodate a suitable hybrid gel matrix (36) adapted for horizontal electrophoresis. Referring in particular to FIG. 6, the first gel portion (37) of the hybrid gel (36) is provided at a longitudinal end of chamber (30) closest to intermediate wall (19), and enables a relatively stable well structure comprising one and preferably a plurality of wells (39) to be provided for accepting samples that are to undergo electrophoresis. The second gel portion (38) is accommodated between the first gel portion (37) and end wall (16).

The wells (39) may be formed by a comb (80), for example, having teeth (84) that are typically inserted into the first gel portion (37) via corresponding apertures (52) comprised in the cover (50). Alternatively, a common slit may be provided in the cover (50) in place of the individual apertures (52). Typically, the comb (80) is kept in place engaged with respect to the cover (50) until the cassette (1) is used, whereupon samples may be introduced into one or more wells (39) via corresponding apertures (52). After use, and before disposing of the cassette (1), the apertures (52) are preferably again closed by means of the comb (80).

The agarose/acrylamide hybrid gel (36) is preferably provided precast in the first chamber (30). In any case, the agarose/acrylamide gel according to the present invention may be formed by introducing a temporary transverse retaining wall (not shown) within chamber (30), displaced longitudinally with respect to intermediate wall (19) to define a subchamber therebetween into which agarose gel is poured and set. Next, the temporary retaining wall is removed, and acrylamide gel is poured into the remainder of the first chamber (30) to the same level as the agarose in the first gel portion (37) to form the second gel portion (38). Another method of casting the agarose/acrylamide hybrid gel is by turning the cassette (1) vertically such that the end wall (16) is uppermost. Acrylamide gel is then poured into the chamber (30) up to the required height (which typically corresponds to the horizontal extent of the acrylamide when the cassette (1) is returned to its horizontal position). Then, with the cassette (1) still in the vertical position, agarose is poured into the chamber (30) until the latter is filled as required. With this method, the acrylamide and agarose gels may be poured into the chamber via apertures (51) and (53), respectively, or both via aperture (53). Other ways of casting the hybrid gel are also possible. Wells (39) may be formed in the normal manner using, for example, a comb (80).

However, the step of casting the hybrid gel matrix (36) is usually performed after the second gel matrix (48) is cast, which is typically performed after the gels (69) and (79) are cast, as described hereinbelow.

In the preferred embodiment of the apparatus according to the present invention, a first acrylamide barrier (90) is optionally provided for preventing contact between the acrylamide portions of the hybrid gel (36) and the external environment, particularly during handling of the cassette (1) and disposal thereof, while at the same time permitting ionic communication therebetween. Acrylamide, comprised mainly in the second gel portion (38), but also optionally present in the first gel portion (37), is toxic and/or carcinogenic and therefore potentially harmful to the cassette operator and to the environment. Preferably, a second acrylamide barrier (95) is provided at the opposed longitudinal end of the cassette (1).

The first acrylamide barrier (90) is provided in the form of the second chamber (40) as a buffer zone between the acrylamide and the opening (42), thus preventing contact via this opening. Second chamber (40)—which is in open communication with first chamber (30), and at least in ionic communication therewith when both chambers are accommodating gels—is provided with any suitable acrylamide barrier material, such as agarose gel, or agar gel for example, or any other suitable safety gel material. Preferably, the first acrylamide barrier extends into the second leg (70).

A second acrylamide barrier (95) is provided at the other longitudinal end of the cassette (1) as a buffer zone between the acrylamide and the opening (32), thus preventing contact via this opening. The second trap (95) is economically provided by the hollow leg (60), which comprises agarose gel, for example, or any other suitable barrier material.

Thus, even if openings (76) and (66) in legs (70) and (60), respectively, remain unsealed, the acrylamide comprised in the hybrid gel (36) is not exposed to the external environment.

The acrylamide barriers (90), (95) are generally prepared before casting the hybrid gel (36) in the first, electrophoresis, chamber (30). With the cover (50), including portion (55) off, and with the bottom ends of the legs (60) and (70) sealed with suitable adhesive peel-off tape, agarose gel (79), or another suitable barrier substance is poured into leg (70) and chamber (40), up to the level of the upper part (11) of base (10). Concurrently or subsequently, agarose gel (69), or another suitable barrier substance is poured into leg (60) preferably up to the level of the upper part (11) of base (10). When the gels (79) and (69) are set, the agarose/acrylamide hybrid gel (36) may be poured and set in the first chamber (30) as hereinbefore described.

Alternatively, a simpler cassette (1) may be provided without the first acrylamide barrier (90), and indeed the second acrylamide barrier (95), if it is so desired.

In such a cases, the cassette (1) may be provided without the second chamber (40) leading to a simplified structure. Thus the base (10) only comprises upper portion (11), the side walls (12), (14) do not include the shorter side wall portions (12'), (14'), respectively, and the intermediate wall (19) is replaced by end wall (18). Similarly, upper wall (55) is not required.

While the first acrylamide barrier (90) has been described as being in the form of a second chamber (40) at a level below that of the first chamber (30), optionally further comprising leg (70), and accommodating a suitable barrier substance, this need not generally be so. Similarly, the second acrylamide barrier, while described for the preferred embodiment as being in the form of leg (60) comprising a suitable barrier substance, this also need not necessarily be so. Minimally, the first acrylamide barrier (90) and the second acrylamide barrier (95) each need only to be adapted to provide ionic communication between the outside of the cassette (1), via leg (70) and leg (60) respectively, and the hybrid gel (36) comprised in the first chamber (30), and comprise a suitable barrier material between the outside of the cassette (1) and the acrylamide in the hybrid gel (36), typically the second portion (38) thereof. Any configuration of first acrylamide barrier (90) and/or of the second acrylamide barrier (95) meeting these criteria is/are generally suitable. Thus, in a more simplified cassette, for example, a single chamber is provided, in which one end thereof, and preferably both ends thereof, are each provided with a barrier material such as agarose gel, for example, juxtaposed with and in communication with hybrid gel accommodated within the chamber for electrophoresis. Thus, while the first acrylamide barrier (90) comprises second chamber (40) as well as the leg (70), optionally a simpler cassette (1) may be provided without the second chamber (40), if it is so desired.

Further optionally, the cassette (1) may also be provided without the said hollow legs (60) and (70), leading to a further simplified structure. Thus communication between said first chamber (30) and external ionic solutions is via opening (32) and opening (42) in the base (10).

Figure 7:
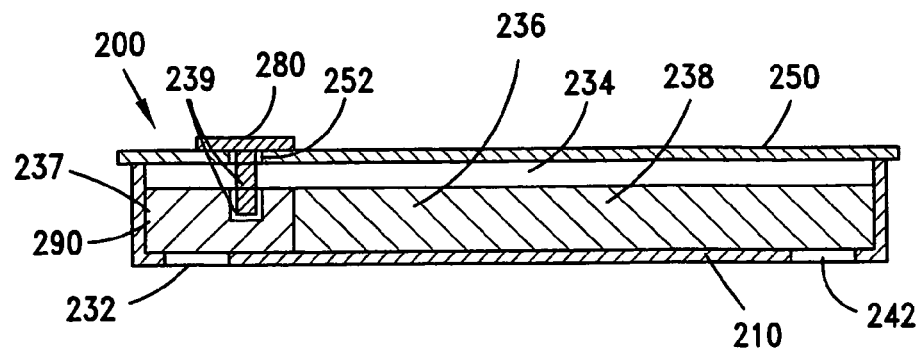
FIG. 7 shows in side elevational cross-sectional view, a second embodiment of the apparatus of the present invention.

Thus, referring to FIG. 7, a second embodiment of the apparatus of the present invention comprises a housing (200) having a base (210) and peripheral walls joined thereto at a lower end thereof, to define a chamber (234). A hybrid gel matrix (236), similar to the hybrid gel matrix (36) of the first embodiment, mutatis mutandis, is accommodated in the chamber (234). The chamber (234) comprises openings (232) and (242) at longitudinal ends of the base (210) for providing ionic communication between the hybrid gel matrix (236) and one common (or a pair of spaced) external buffer solution. Wells (239) are provided in the hybrid gel matrix (236) for introducing samples to be electrophoresed. Optionally, a cover plate (250) may be provided, having suitable openings (252) for a comb (280) to be inserted therein to form wells (239). In this embodiment, the first portion (237) of the hybrid gel (236) also acts as a first acrylamide barrier (290).

Figure 8:
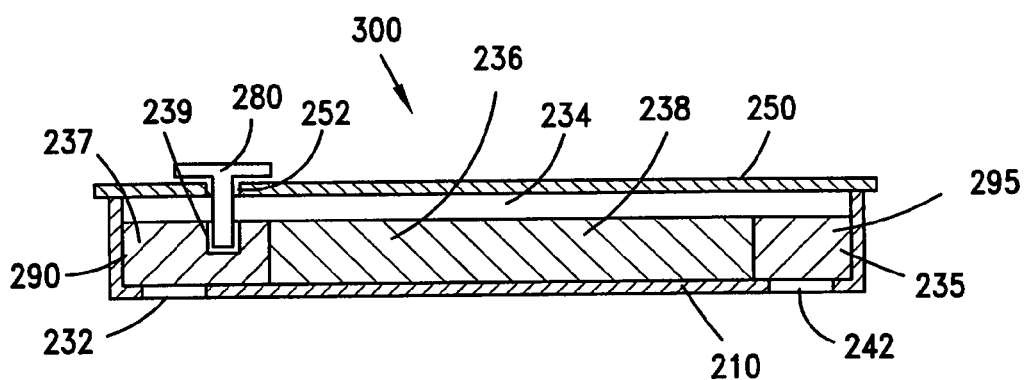
FIG. 8 shows in side elevational cross-sectional view, a third embodiment of the apparatus of the present invention.

A third embodiment of the present invention comprises a housing (300) having all the components of the second embodiment as described above, mutatis mutandis, and is illustrated in FIG. 8. In addition, though, the chamber (234) further comprises a second acrylamide barrier (295) in the form of a third gel portion (235) juxtaposed and in ionic communication with the hybrid gel matrix (236), but located at the opposed longitudinal end of the housing (200) with relation to the first gel portion (237) of the hybrid gel (236). The third gel matrix (235) comprises a suitable barrier substance and provides for ionic communication between the hybrid gel (236) and the outside of the chamber (234) via opening (242).

Figure 9:
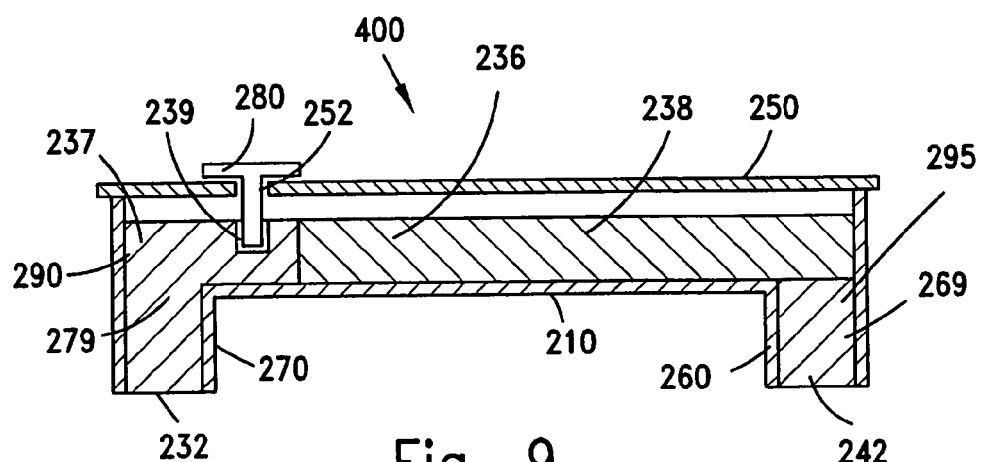
FIG. 9 shows in side elevational cross-sectional view, a fourth embodiment of the apparatus of the present invention.

A fourth embodiment of the present invention comprises a housing (400) having all the components of the second embodiment as described above, mutatis mutandis, and is illustrated in FIG. 9. In addition, though, the chamber (234) further comprises a pair or leg members (270), (260), which downwardly extend the openings (32), (42) respectively, similar to the leg members (70) and (60), respectively, of the preferred embodiment, mutatis mutandis. The first acrylamide trap (290) may thus be independent of the first gel portion (237) of the hybrid gel (236), and be comprised in the leg (70) in the form of a suitable barrier material (279) such as agarose, and this may be so in applications in which the first gel portion (237) may also comprise some acrylamide. Alternatively, the first acrylamide barrier (290) may comprise both the first portion (237) of the hybrid gel (236) together with agarose or similar barrier substance (279) in leg (70). The second acrylamide barrier (295) may be in the form of a fourth gel portion (269) juxtaposed and in ionic communication with the hybrid gel matrix (236), but located within leg (60) at the other longitudinal end of the housing (200) with relation to the other leg (270). The fourth gel matrix (269) thus comprises a suitable barrier substance and provides for ionic communication between the hybrid gel (236) and the outside of the chamber (234) via opening (242).

Figure 10A:
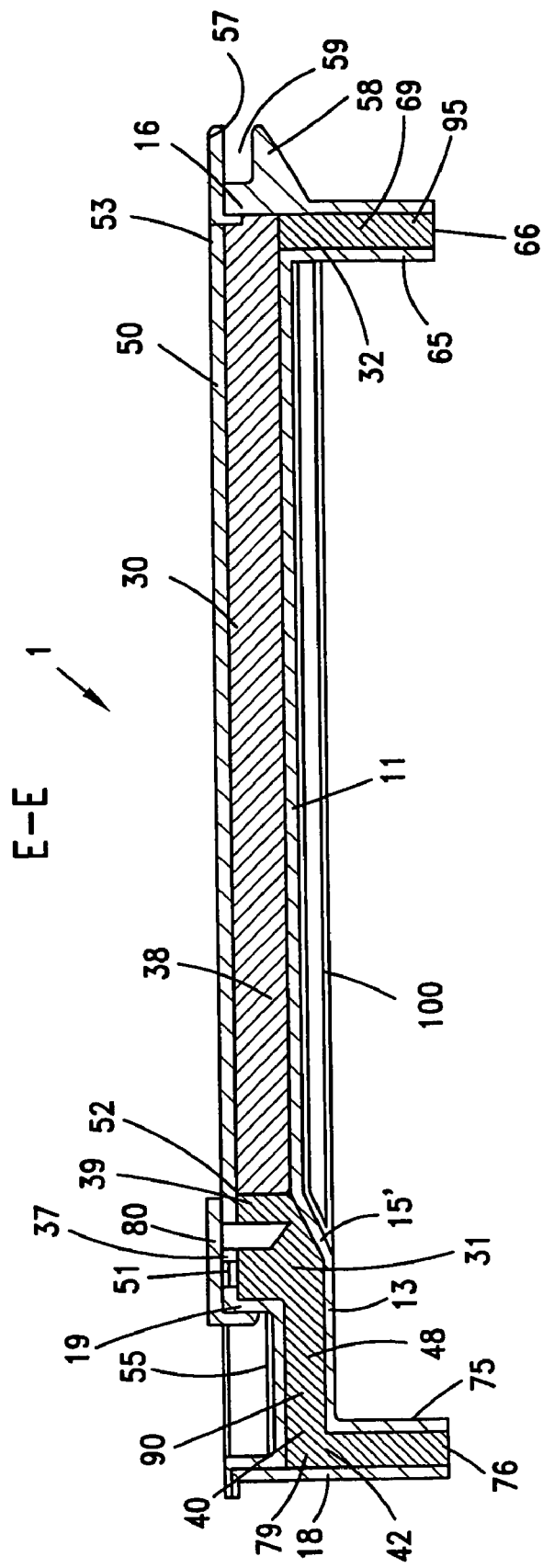
FIGS. 10a and 10b show in side elevational cross-section view, a fifth embodiment of the apparatus of the present invention.
Figure 10B:
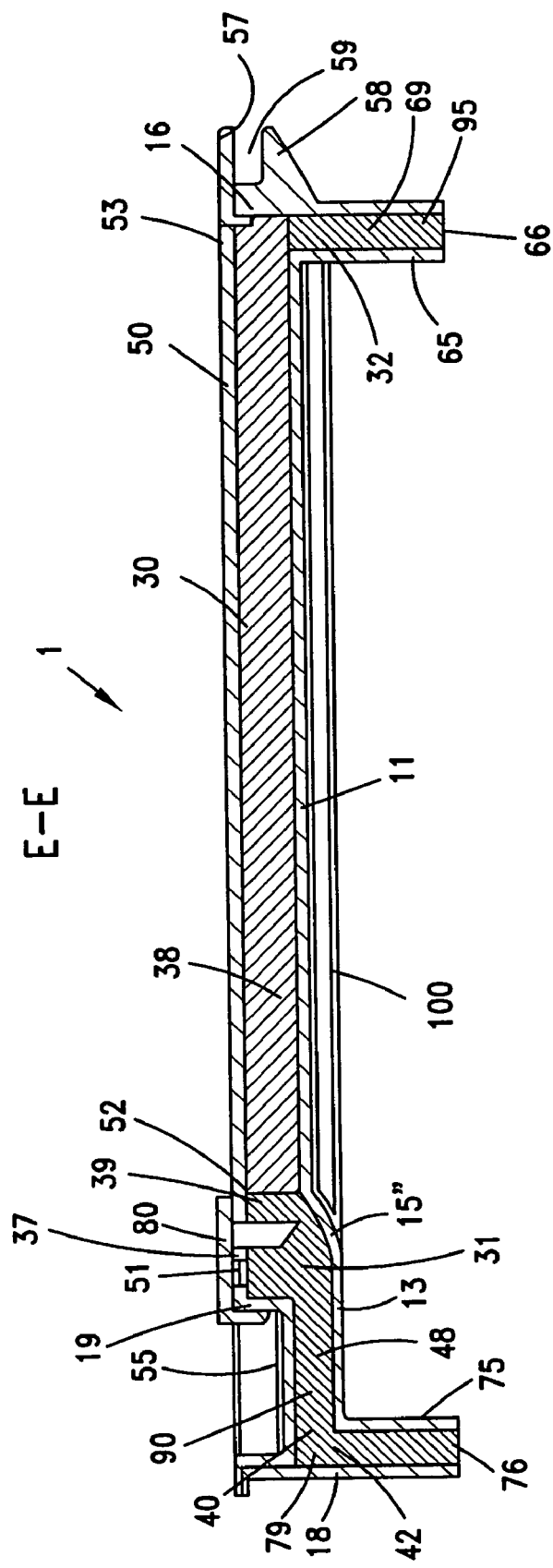

A fifth embodiment of the present invention is illustrated in FIGS. 10a and 10b, and comprises a housing 1 having all of the components of the first embodiment as described above, mutatis mutandis, with the following differences. In this embodiment, upper part (11) and lower part (13) of the stepped base (10) can be joined longitudinally one to the other by a first intermediate wall that is situated in a manner other than vertical, such as a wall that is positioned on an incline (15') (FIG. 10a) from lower part (13) toward upper part (11), or alternatively, that ascends arcuately (15") (FIG. 10b) from lower part (13) toward upper part (11). In either case, the point of meeting between the non-vertical first intermediate wall and the upper part (11) must be located below the second gel matrix, preferably such that the well (39) is positioned at least partially above the non-vertical intermediate wall.

This embodiment may be preferred when it is desired to use large sample volumes in the electrophoresis. Large sample volumes are desired when the material from which the sample was prepared contains a low concentration of relevant molecule, wherein said material is, for example, but not restricted to, a piece of tissue, small organisms, DNA, RNA or proteins. Large volume samples improve the possibility of detecting the relevant molecule by increasing the amount of molecules in the sample, overcoming the detection threshold of the gel. When area 31 is enlarged, the size of the well can be enlarged as well. A larger well size allows the use of larger sample volumes to be loaded into the gel. Thus, as demonstrated for example, by FIG. 12, more molecules will be present in the low concentration sample, which allows for easier detection when using a simple and fast separation method.

While the hybrid gel and the apparatus for accommodating the same according to the present invention have been described herein with reference to horizontal gel electrophoresis, the present invention is not limited thereto, and can be applied to other forms of electrophoresis including vertical electrophoresis as well as two dimensional gel (2D gel), mutatis mutandis.

While in the foregoing description describes in detail only a few specific embodiments of the invention, it will be understood by those skilled in the art that the invention is not limited thereto and that other variations in form and details may be possible without departing from the scope and spirit of the invention herein disclosed.

EXAMPLES

Experimental Procedures
 Buffers and reagents
 *Protein extraction buffer:
 B-PER™ Bacterial Protein Extraction Reagent from PIERCE (Cat#. BI45492)
 *Sample buffer X1:
 62 mM Tris-HCl, pH 6.8, 2% SDS, 5% 2-☐ Mercaptoethanol, 10% Glycerol, 0.01%(w/v) Bromophenol Blue.
 *Running buffer X1:
 25 mM Tris Base, 192 mM Glycine, 0.1% SDS
 *staining buffer/wash buffer:
 SeeBand Forte protein staining from Gene BioApplication (Cat#. SB020) was used.
 *BSA—purchased from Sigma (Cat#. B-4287).
 *Lysozyme—purchased from Sigma (Cat#. L-7651).
 *Markers—purchased from Fermentas (Cat#. SM0671).
 Sample preparation
 The samples were prepared by addition of one volume of 2X sample buffer to the sample and heating to 90° C. for 5 minutes.
 The *E. Coli* extract was prepared according to the manufacturers instruction (PIERCE).
 *Preparation of gels, 10% and 12%:
 Gel solution was prepared by combining the following components in an aqueous solution in the concentration indicated (all components were purchased from Sigma):
 *10% Resolving gel: 10% acrylamide/bisacrylamide (37.5:1), 0.375M Tris-HCl, pH 8.8, 0.08% ammonium persulfate, 0.05% TEMED.
 *12% Resolving gel: 12% acrylamide/bisacrylamide (37.5:1), 0.375M Tris-HCl, pH 8.8, 0.08% ammonium persulfate, 0.05% TEMED.

*4% Stacking gel: 4% acrylamide/bisacrylamide (37.5:1), 0.375M Tris-HCl, pH 6.8, 0.08% ammonium persulfate, 0.1% TEMED.

Gel solutions were placed in the cassette described above. The gels were allowed to polymerize at room temperature for about one hour.

After loading the samples gels were run at 100V for about two hours.

Coomassie blue staining

The coomassie blue staining was performed according to the manufacturers instructions (Gene Bio-Application).

The following examples demonstrate the high quality resolution performance of the pre cast gels of the invention and the advantage of using horizontal acrylamide gels for electrophoresis.

Example 1

Figure 11:
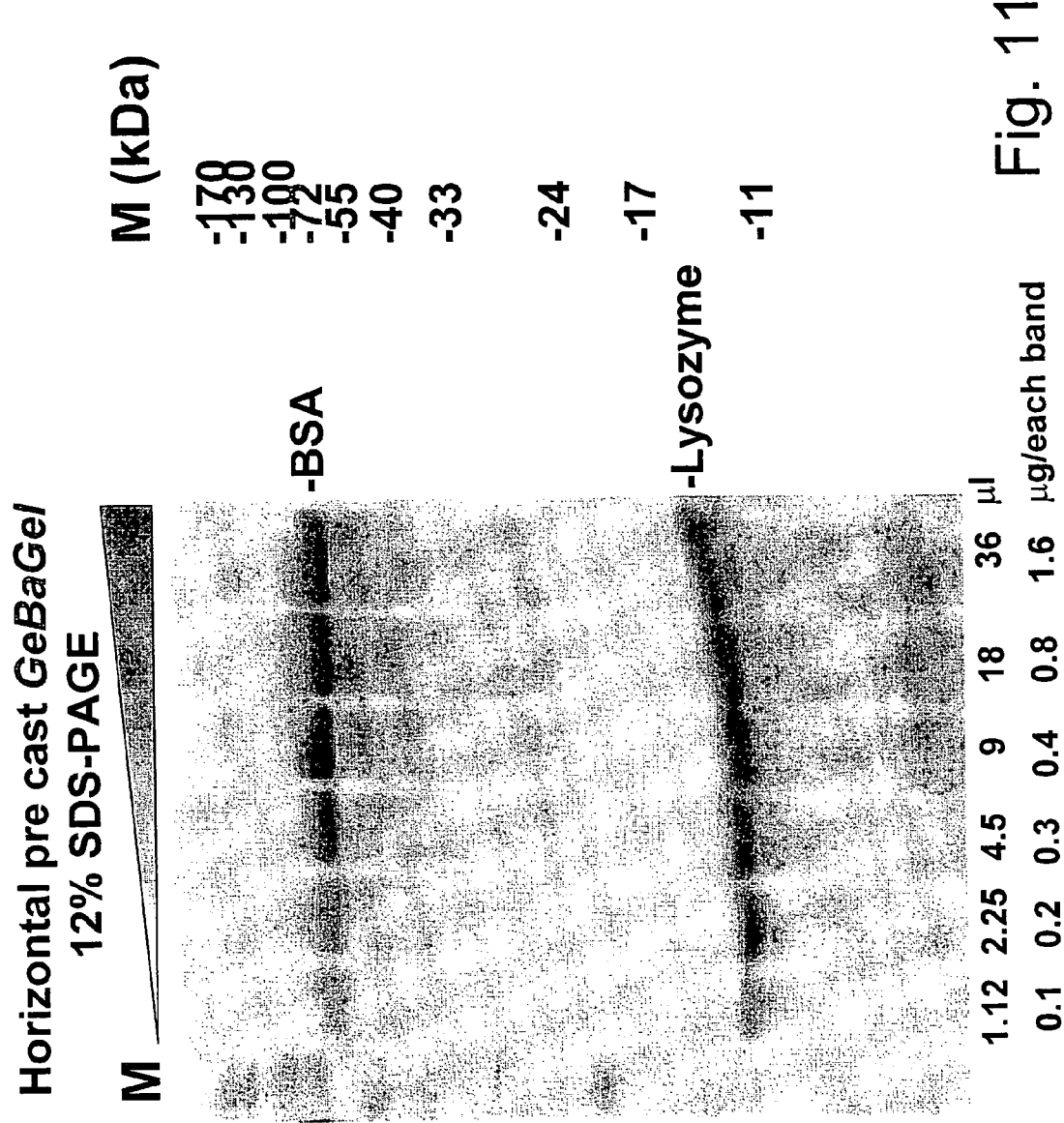
FIG. 11 shows the quantitative and qualitative advantages of horizontal PAGE gels and the effect of sample volume on the experiment results. Different sample volumes (as indicated therein) of bovine serum albumin (BSA) and lysozyme (lanes 2-7) were separated on a horizontal pre cast 12% SDS PAGE GeBaGel of the invention. Gels were subjected to Coomassie blue staining.

This Example illustrates the quantitative influence of large samples on the experiment results quality. Protein samples from a prokaryote source were prepared as described in experimental procedures and loaded on a 12% SDS PAGE GeBaGel of the invention (FIG. 11). Incremental amounts of BSA and lysozyme were loaded on the gel for illustrating the minimal quantity/volume of loaded sample needed for appropriate visualization. Following separation of protein samples, gels were subjected to Coomassie blue staining. The quantitative effect is reflected by the gel band intensity and band width. As demonstrated by the figure, bands reflecting the BSA or lysozyme samples were clear when at least amount of 0.4 μg protein was loaded on the gel (lane 5). Thus, clearer results are obtained when larger sample amount is loaded. Therefore, combining good resolution with the ability to load large samples, permitted by the special design of the wells, may improve significantly the experimental outcome.

Large sample volume is needed when the material source is highly diluted or when the molecule of interest is found in a very low amount in the material analyzed.

FIG. 12, demonstrates another example of quantitative influence of large sample volume, on the experiment results quality when visualization of proteins found in low amount in a sample, is desired.

Human serum samples were loaded on the 10% SDS PAGE GeBaGel of the invention, in three different sample volumes (FIG. 12, lanes 1-3). Known amounts of BSA and lysozyme, were loaded on the gels (FIG. 12, lanes 5-9) and served as controls for estimating the protein sample volume needed for clear visualization of a desired protein band. As clearly demonstrated by FIG. 12, for this gel percentage (10%), the minimal volume of the control samples visualized was 9 μl (0.8 μg protein, lanes 7-9). Bands reflecting the control proteins were hardly detected in lanes that were loaded with smaller volume (lanes 5-6).

It should be further noted that the quantitative effect is more prominent in samples of mixed molecules (e.g. tissues, extracts, medium, serum, etc.) compared to isolated molecules. Therefore, the use of gels with high loading volume wells that accommodate large amount of material without compromising resolution should be of great advantage for scientific research and routine laboratory tests.

Example 2

This Example illustrates the quantitative influence of large samples on the experiment results quality. Incremental volumes (5 μl-30 μl) of protein samples from a prokaryote source (E. coli) were prepared as described in experimental procedures. Samples were loaded on a 10% SDS PAGE GeBaGel of the invention. Following separation of proteins, the gel was subjected to coomassie blue staining, for visualization of protein bands. As clearly demonstrated by FIG. 13, many bands reflecting different proteins in the sample, cannot be detected when small volume is applied. These bands (marked with asterisks) are visualized only when large volume of sample, is loaded on the gel.

While this invention has been described in terms of some specific examples, many modifications and variations are possible. It is therefore understood that within the scope of the appended claims, the invention may be realized otherwise than as specifically described.

What is claimed is:

1. An apparatus for performing electrophoresis therein, comprising:
    a housing including a base and peripherally joined walls defining a first chamber having a first longitudinal end and a second longitudinal end;
    a solidified hybrid gel for horizontal electrophoresis of a sample within an acrylamide gel, said hybrid gel including a substantially solidified first gel portion in communication with a substantially solidified second gel portion, said solidified first gel portion having at least sufficient agarose for enabling accommodation therein of the sample for an electrophoresis process after said first gel portion is solidified, and said second gel portion being made substantively from acrylamide and enabling the electrophoresis process to be applied within said second gel portion to the sample accommodated in said first gel portion, said solidified hybrid gel being accommodated in said first chamber and arranged such that migration occurs in a direction from said second end to said first end when said device is used in the electrophoretic process;
    said base having formed therein a first opening and a said second opening respectively at said first and second longitudinal ends thereof, each of said openings being adapted to permit ionic communication between said gel and an external ionic buffer solution; and
    substantially hollow first and second transverse legs downwardly depending therefrom at said first and second longitudinal ends thereof, respectively, said first and second legs including a suitable third gel portion and a suitable fourth gel portion, respectively, communicating with said first chamber via said corresponding openings, said first and second legs having open bottom ends.

2. The apparatus as claimed in claim 1, wherein said first gel is made substantially from agarose.

3. The apparatus as claimed in claim 1, further comprising the third gel portion juxtaposed with said second gel portion at an end thereof opposed to said first gel portion, wherein said third portion comprises agarose.

4. The apparatus as claimed in claim 1, wherein said first gel portion is adapted for accommodating therein at least one sample for electrophoresis by means of at least one corresponding well formed in said first gel portion.

5. Apparatus as claimed in claim 1, further comprising a first acrylamide barrier in communication with said first opening for substantially preventing contact between at least said second portion of said hybrid gel and an outside of the apparatus via said first opening.

6. Apparatus as claimed in claim 5, further comprising a second chamber juxtaposed and in communication with said first chamber, said second chamber adapted for providing at least part of said first acrylamide barrier.

7. Apparatus as claimed in claim 6, wherein said second chamber comprises a fifth gel portion.

8. Apparatus as claimed in claim 7, wherein said fifth gel portion comprises agarose.

9. Apparatus as claimed in claim 1, further comprising a first acrylamide barrier in communication with said first opening for substantially preventing contact between at least said second portion of said hybrid gel and an outside of the apparatus via said first opening.

10. Apparatus as claimed in claim 9, wherein said first acrylamide barrier is provided by said third gel portion comprised in said first leg.

11. Apparatus as claimed in claim 9, wherein said third gel portion comprises agarose.

12. Apparatus as claimed in claim 1, wherein the base further comprises a lower part and an upper part, thereby defining a stepped bottom base.

13. Apparatus as claimed in claim 12, wherein the lower part is joined longitudinally to the upper part by an intermediate wall.

14. Apparatus as claimed in claim 13, wherein the intermediate wall is perpendicular to the lower part of the base.

15. Apparatus as claimed in claim 13, wherein the intermediate wall is positioned at an incline from the lower part of the base to the upper part of the base.

16. Apparatus as claimed in claim 13, wherein said intermediate wall ascends arcuately from the lower part of the base to the upper part of the base.

17. Apparatus as claimed in claim 13, wherein the intermediate wall meets die upper part of the base at a point on said base that is located below the second gel matrix.

18. Apparatus as claimed in claim 1, further comprising a second acrylamide barrier in communication with said second opening for substantially preventing contact between at least said second portion of said hybrid gel and an outside of the apparatus via said second opening.

19. Apparatus as claimed in claim 18, wherein said second acrylamide barrier is comprised by a sixth gel portion interposed between said second gel portion of said hybrid gel and said second opening, said sixth gel portion being comprised substantially of agarose.

20. Apparatus as claimed in claim 18, wherein said second acrylamide barrier is provided at least in part by said fourth gel portion comprised in said second leg.

21. Apparatus as claimed in claim 18, wherein said fourth gel portion comprises agarose.

22. Apparatus as claimed in claim 18, wherein said second acrylamide barrier is comprised of the same material as said first gel portion of said hybrid gel, said first portion being comprised substantially of agarose.

23. Apparatus as claimed in claim 1, further comprising a cover for releasably closing at least said first chamber.

24. Apparatus as claimed in claim 23, further comprising a suitable comb for forming wells, said cover comprising at least one suitable aperture for enabling said comb to penetrate into said first gel portion.

25. Apparatus as claimed in claim 23, wherein said cover comprises a tab in registry with and spaced from a platform comprised at said first longitudinal end of said apparatus.

26. Apparatus as claimed in claim 1, further comprising suitable adhesive strips for reversibly sealing said bottom ends of said first and second legs, respectively.

27. Apparatus as claimed in claim 1, wherein said base and said first and second legs are adapted to enable said apparatus to be used with standard electrophoresis devices having a pair of parallel juxtaposed buffer-containing troughs separated by an elevated platform for supporting the said base, said first and second legs extending sufficiently into corresponding said troughs to provide ionic communication at least between said third gel portion and buffer contained in one trough, and between said fourth gel portion and buffer contained in the other trough.

28. A method for providing a solidified hybrid gel for horizontal electrophoresis of a sample within an acrylamide gel, said hybrid gel including a substantially solidified first gel portion in communication with a substantially solidified second gel portion, said solidified first gel portion having at least sufficient agarose for enabling accommodation therein of the sample for an electrophoresis process after said first gel portion is solidified, and said second gel portion being made substantially from acrylamide to enable the electrophoresis process to be applied within said second gel portion to the sample accommodated in said first gel portion, the method which comprises the steps of:
  providing a closed tray having a pouring aperture, and turning the tray vertically such that the aperture is uppermost;
  pouring said first gel portion via said aperture up to a required height therein and allowing said first portion to set;
  pouring said second gel portion therein up to the top of the tray, and allowing said second portion to set;
  returning said tray to a horizontal orientation.

29. Method as claimed in claim 28, further comprising the step of forming at least one well in said first gel portion.

30. Method as claimed in claim 29, wherein said at least one well is formed by means of a comb, via suitable apertures in the tray.

31. Method as claimed in claim 29, wherein said at least one well is formed by means of a comb by first removing an upper cover of the tray.

32. A method for providing a solidified hybrid gel for horizontal electrophoresis of a sample within an acrylamide gel, said hybrid gel including a substantially solidified first gel portion in communication with a substantially solidified second gel portion, said solidified first gel portion having at least sufficient agarose for enabling accommodation therein of at least one sample for electrophoresis after said first gel portion is in solidified form, and said second gel portion being made substantially from acrylamide to enable the electrophoresis process to be applied within said second gel portion to the sample accommodated in said first gel portion, the method which comprises the steps of:
  providing an open tray;
  providing a temporary transverse retaining wall within the tray, displaced longitudinally with respect to one longitudinal end thereof, to define a subchamber therebetween;
  pouring said first gel portion into said subchamber and allowing the first gel portion to set;
  removing the temporary retaining wall;
  closing the tray with a suitable cover having a suitable aperture;
  pouring the second gel portion into the remainder of the tray via said aperture and allowing the second gel portion to set.

33. Method as claimed in claim 32, further comprising the step of forming at least one well in said first gel portion.

34. Method as claimed in claim 33, wherein said at least one well is formed by means of a comb, via suitable apertures in the tray.

35. Method as claimed in claim 34, wherein said at least one well is formed by means of a comb by first removing an upper cover of the tray.

36. A method for performing a horizontal electrophoresis process on a sample, which comprises the steps of:

providing a solidified hybrid gel for the horizontal electrophoresis process of the sample within an acrylamide gel, said hybrid gel including a substantially solidified first gel portion in communication with a substantially solidified second gel portion, said solidified first gel portion having at least sufficient agarose for enabling accommodation therein of the sample for electrophoresis process after said first gel portion is solidified, and said second gel portion being made substantially from acrylamide to enable the electrophoresis process to be applied within said second gel portion to the sample accommodated in said first gel portion, said first gel portion having a well formed therein, said well being adapted to receive a corresponding sample;

accommodating said gel matrix in a suitable horizontal electrophoresis chamber;

accommodating said at least one sample within a corresponding at least one well in said first gel portion;

providing suitable buffer solution to said chamber;

providing a suitable electric potential to said chamber such as to activate the electrophoresis process.

37. Method as claimed in claim 36, wherein said sample comprises small fragments of nucleic acids including at least one of DNA and RNA.

38. Method as claimed in claim 36, wherein said sample comprises at least one suitable protein.

* * * * *